March 10, 1936. L. BALDERSTON, 3D Plant Pat. 168
APPLE TREE
Filed Oct. 29, 1935
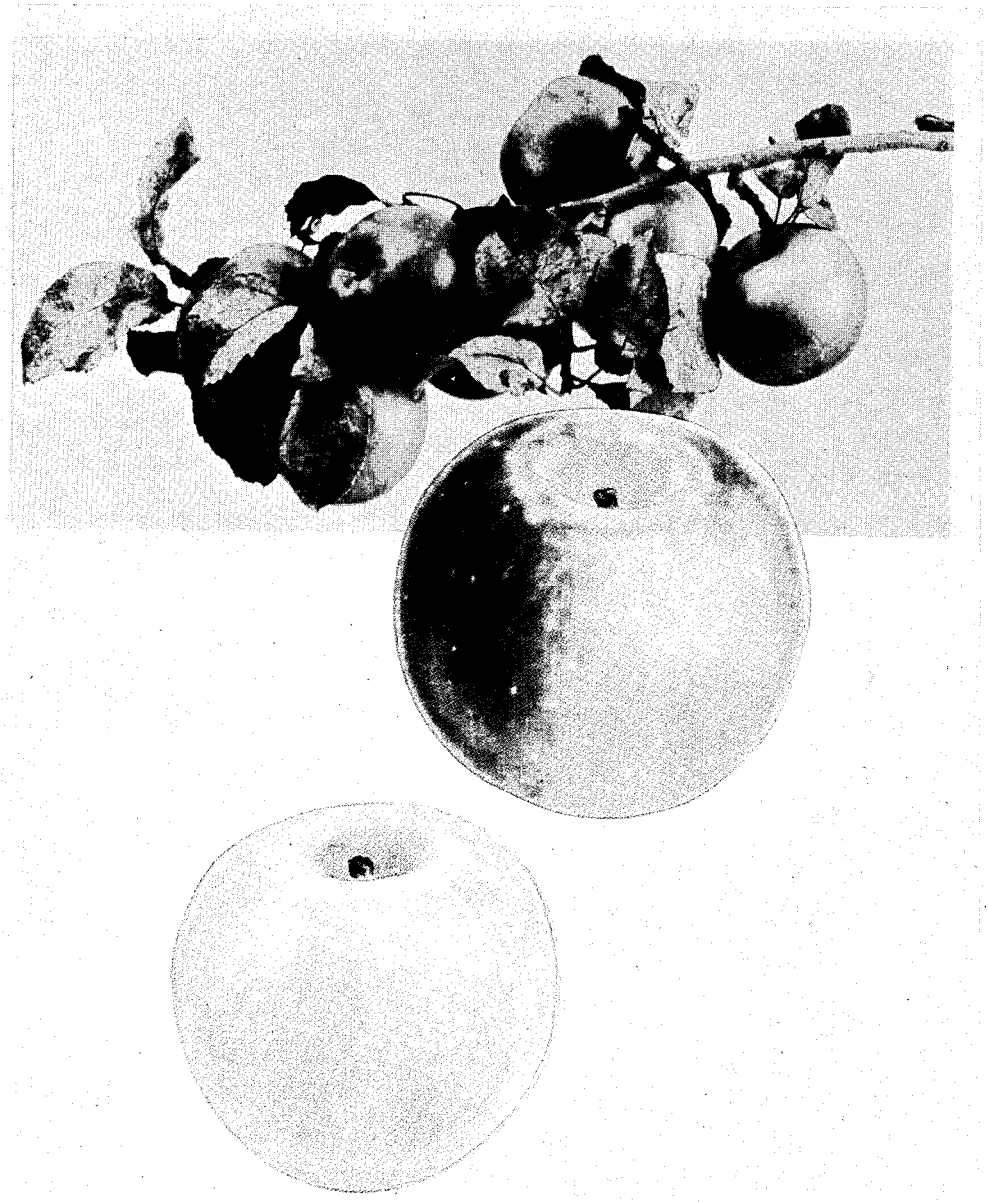
Inventor
Lloyd Balderston III
By Robbs & Robbs
Attorneys Patented Mar. 10, 1936

Plant Pat. 168

UNITED STATES PATENT OFFICE

168

APPLE TREE

Lloyd Balderston, 3d, Colora, Md., assignor to
Bountiful Ridge Nurseries, Princess Anne, Md.

Application October 29, 1935, Serial No. 47,321

1 Claim. (Cl. 47—62)

The present discovery relates to a new and distinct variety of apple tree, a red bud sport of the well known commercial York Imperial.

The fruit of this improved type of York is characterized by its high or bright red color as compared with the normal type and by the fact that this color develops at least two weeks earlier than the known variety grown under comparable conditions.

It is to be understood that the original tree representing this new variety was discovered as a single tree in an orchard of York Imperials planted as such and it possesses in all respects the same characteristics as the York Imperial excepting as regards the color and coloring of the fruit. Careful examination indicates that the entire tree is a bud sport of the regular York Imperial and asexual reproductions from the original tree show that the varietal distinctions above mentioned are transmitted to the progeny.

Taking the present season as a basis for comparison of the varietal distinctions, the present mutation started to color about August 1, whereas the surrounding York Imperials started to put on their first color about August 12, nearly two weeks later, and in picking specimens of apples from the new variety on September 2, the fruit on the entire tree was sufficiently colored to more than pass the U. S. #1 grade, whereas hardly any fruit on the adjoining York Imperials could pass that grade.

In further reference to the coloring of the fruit, it is notable that the present sport presents a solid (or blushed) red color, whereas the ordinary York is striped. The comparison between the new variety sport and the regular York Imperial is clearly shown in the drawing annexed hereto in which the upper illustration of the apple in color is a reproduction of the new variety and the lower illustration illustrates a specimen of the regular York.

The drawing also includes a reproduction of a branch of the new variety showing the grouping of the apples and the foliage of the tree.

The specimens hereinafter described were grown at Colora, Maryland, where the picking was made on October 7, 1935, though the fruit showed sufficient coloring for picking on September 27, 1935.

The following is a detail description of the new variety, all references to color being in accordance with the Munsell Color System.

Tree:
- Large to medium,
- Medium to vigorous,
- Upright and spreading,
- Tall,
- Open, round-topped,
- Rapid growing,
- Half-hardy,
- Productive,
- Biennial bearing.

Trunk:
- Stocky,
- Shaggy.

Branches:
- Thick,
- Shaggy,
- Much branching,
- Brown to grey color.

Lenticels—
- Medium number,
- Medium size.

Leaves:
- Length—3¼ inches,
- Width—2⅛ inches,
- Medium size,
- Medium width,
- Medium length,
- Oval to ovate,
- Abruptly pointed,
- Thick,
- Medium to dark green color,
- Rugose.

Margin—
- Crenate,
- Coarsely serrate.

Petiole—
- Length—⅞ inch,
- Medium to short,
- Medium thickness.

Flowers:
- Dates of first and full bloom varies from season to season and location; same as Golden Delicious and York Imperial; 3 days later than Staymans, Grimes, Wealthy and Delicious.
- Medium size,
- Pink to white color.

Fruit:
Maturity when described—Eating hard, underripe,
Date—September 9, 1935 to September 27, 1935.
Size:
Uniform to variable,
Axial diameter—2½ inches,
Transverse—2¾ inches.
Form:
Irregular,
Oblique,
Oblate,
Ribbed.
Cavity—
Symmetrical, rounded,
Flaring toward apex,
Acute to acuminate,
Even, undulate,
Depth—⅝ inch,
Breadth—1¼ inches,
Markings—green and partly russeted.
Basin—
Symmetrical to unsymmetrical,
Abrupt at base to rounded,
Wide, furrowed, glabrous,
Depth—¼ inch,
Breadth—$1\frac{3}{16}$ inches.
Stem:
Medium, pubescent,
Length—½ inch,
Breadth—$\frac{3}{32}$ inch,
Markings—green—pubescent.
Calyx:
Open to closed,
Segments persistent,
Broadly-lanceolate,
Acuminate,
Length—$\frac{3}{16}$ inch approximately,
Ascending, approximate,
Reflexed from base at apex,
Pubescent outer surface,
Pubescent inner surface.
Eye:
Medium size,
Partially closed.
Skin:
Thick, tough, smooth,
Glossy, waxed.
Dots—conspicuous, many, large and small, even and raised, sometimes ruptured, aerolar and angular-stellate.
Color of dots—light and russet.
Distribution of dots——few at cavity, more concentrated at apex.
Ground color—light yellow to green.
Color markings — mottled, self - colored, bright.
Color of markings—solid color. Scarfskin at cavity.
Bloom—scant.
Scarfskin—gray-white, light, distribution at cavity.
General color effect—medium to bright solid red.
Flesh:
Rather dry.
Color of flesh—satiny, white with yellowish tint.
Texture—firm, little coarse, crisp.
Flavor—subacid, mild; sprightly.
Aroma—distinct.
Quality—good.
Core:
Median, distant.
Bundle area (longitudinal section)—medium, broadly ovate, symmetrical to unsymmetrical at base; in bundle alternate with cell.
Halves of area—unequal.
Bundles—green, conspicuous, in two whorls.
Alternate bundle—approximate to calyx—tube, reaches tube below stamens.
Core lines—clasping.
In cross section—distinct.
Carpellary area—indistinct, large.
Calyx-tube—pubescent, apex funnel-form.
Stem entire depth—¾ inch.
Styles—present, distinct and pubescent toward base, apex at point of branching throughout.
Stamens—in one whorl, basal, median.
Auxiliary cavity—present.
Seed cells—axile, open.
Cell walls—approximate, thin, tough.
Length—approximately ¾ inch.
Breadth—$\frac{7}{16}$ inch.
Longitudinal section—broadly ovate, obtuse at apex.
Surface—fissured, tufted.
Cross section—broad to narrow.
Seeds:
Number perfect—350.
Imperfect—68.
Largest—⅜ inch by ¼.
Number in one cell—2.
Length—$\frac{11}{32}$ inch.
Breadth—$\frac{7}{32}$ inch.
Form—acuminate, obtuse.
Color—medium brown.
Use:
Market, culinary.
Keeping quality:
Good.
Number of days in ordinary storage—October to March and as late as July.
Resistance to:
Insects—good to medium.
Diseases—good to medium.
Same as York.
I claim:
A new and distinct variety of apple tree, as shown and described, characterized by the bright red solid or blushed color of its fruit and the early development of such coloring.

LLOYD BALDERSTON, III.